United States Patent
Crowther et al.

(10) Patent No.: US 10,538,604 B2
(45) Date of Patent: Jan. 21, 2020

(54) CATALYSTS FOR CONTROL OF LONG CHAIN BRANCHING

(71) Applicant: Univation Technologies, LLC, Houston, TX (US)

(72) Inventors: Donna J. Crowther, Seabrook, TX (US); C. Jeff Harlan, Houston, TX (US); Jackie Lovell, Houston, TX (US); Haiqing Peng, Sugar Land, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 15/566,286

(22) PCT Filed: Apr. 14, 2016

(86) PCT No.: PCT/US2016/027563
§ 371 (c)(1),
(2) Date: Oct. 13, 2017

(87) PCT Pub. No.: WO2016/168479
PCT Pub. Date: Oct. 20, 2016

(65) Prior Publication Data
US 2018/0079838 A1   Mar. 22, 2018

Related U.S. Application Data

(60) Provisional application No. 62/148,922, filed on Apr. 17, 2015.

(51) Int. Cl.
*C08F 4/6592* (2006.01)
*C08F 210/16* (2006.01)
*B01J 31/22* (2006.01)
*C07F 7/08* (2006.01)
*C08F 110/02* (2006.01)
*C08F 210/14* (2006.01)

(52) U.S. Cl.
CPC ....... *C08F 4/65927* (2013.01); *B01J 31/2295* (2013.01); *C07F 7/0803* (2013.01); *C08F 110/02* (2013.01); *C08F 210/14* (2013.01); *C08F 210/16* (2013.01); *C08F 2500/12* (2013.01); *C08J 2323/08* (2013.01)

(58) Field of Classification Search
CPC .............. C08F 4/65927; C08F 4/65912; C08F 4/65916; C08F 210/16
See application file for complete search history.

(56) References Cited

U.S. PATENT DOCUMENTS

2009/0099310 A1   4/2009   Ohtaki et al.
2009/0318644 A1   12/2009   Brant et al.
2014/0194277 A1   7/2014   Ishihama et al.

OTHER PUBLICATIONS

International Search Report & Written Opinion for related PCT Application PCT/US2016/027563, dated Jul. 25, 2016 (11 pgs).
International Preliminary Report on Patentability for related PCT Application PCT/US2016/027563, dated Oct. 26, 2017 (8 pgs).
Mise, et al., "Excellent Stereoregular Isotactic Polymerizations of Propylene with C2-symmetric Silylene-Bridged Metallocene Catalysts"; Chemistry Letters, Chemical Society of Japan, vol. 10, pp. 1853-1856 (Jan. 1, 1989) 4 pgs.

*Primary Examiner* — Caixia Lu
(74) *Attorney, Agent, or Firm* — Brooks, Cameron & Huebsch, PLLC

(57) ABSTRACT

Catalyst systems and methods for making and using the same are disclosed. A catalyst composition is provided that includes a catalyst compound supported to form a supported catalyst system, the catalyst compound including: where each of $R^1$, $R^2$, $R^3$, $R^4$, $R^5$, $R^6$, $R^7$ and X are as discussed herein.

10 Claims, 8 Drawing Sheets

200

CATALYSTS FOR CONTROL OF LONG CHAIN BRANCHING

This application is a National Stage Application under 35 U.S.C. § 371 of International Application Number PCT/US2016/027563, filed Apr. 14, 2016 and published as WO 2016/168479 on Oct. 20, 2016, which claims the benefit to U.S. Provisional Application 62/148,922, filed Apr. 17, 2015, the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution as the reaction temperature is increased, for example, to increase production rates. Further, a single site catalyst will often incorporate comonomer among the molecules of the polyethylene copolymer at a relatively uniform rate. The molecular weight distribution and the amount of comonomer incorporation can be used to determine a composition distribution.

The composition distribution of an ethylene alpha-olefin copolymer refers to the distribution of comonomer, which form short chain branches, among the molecules that comprise the polyethylene polymer. When the amount of short chain branches varies among the polyethylene molecules, the resin is said to have a broad composition distribution (BCD). When the amount of comonomer per 1000 carbons is similar among the polyethylene molecules of different chain lengths, the composition distribution is said to be "narrow".

Further, the composition distribution may have variation in the amount of comonomer incorporated into long chains versus short chains.

The composition distribution is known to influence the properties of copolymers, for example, stiffness, toughness, extractable content, environmental stress crack resistance, and heat sealing, among other properties. The composition distribution of a polyolefin may be readily measured by methods known in the art, for example, Temperature Raising Elution Fractionation (TREF) or Crystallization Analysis Fractionation (CRYSTAF).

It is generally known in the art that a polyolefin's composition distribution is largely dictated by the type of catalyst used and is typically invariable for a given catalyst system. Ziegler-Natta catalysts and chromium based catalysts produce resins with broad composition distributions (BCD), whereas metallocene catalysts normally produce resins with narrow composition distributions (NCD).

In addition to short chain branching, as discussed above, polymer catalysts often generate polymers that have long chain branching. Long chain branching may be useful in some applications, for example, contributing to polymer alignment in processing, which can make the polymer tougher. However, the alignment can also create problems, such as anisotropy in polymer properties. Accordingly, control over long chain branching would be useful.

SUMMARY

An exemplary embodiment described herein provides a method of polymerizing olefins to produce a polyolefin polymer with control over long chain branching, including contacting ethylene and a comonomer with a catalyst system, wherein the catalyst system includes a catalyst compound comprising:

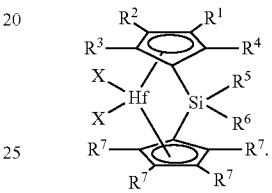

In this formula, $R^1$ is a saturated hydrocarbyl group of at least two carbons in length. $R^2$ is an H, a hydrocarbyl group, a substituted hydrocarbyl group, a heteroatom group, or connects to $R^3$ through a ring structure. $R^3$ is an H, a hydrocarbyl group, a substituted hydrocarbyl group, a heteroatom group, or connects to $R^2$ through a ring structure. $R^4$ is an H or a methyl group. $R^5$ is an H, a hydrocarbyl group, a substituted hydrocarbyl group, a heteroatom group, or forms a ring structure with $R^6$. $R^6$ is an H, a hydrocarbyl group, a substituted hydrocarbyl group, a heteroatom group, or forms a ring structure with $R^5$. Each $R^7$ is independently an H, a hydrocarbyl group, a substituted hydrocarbyl group, a heteroatom group, or connects to an adjacent $R^7$ group through a ring structure. Each X is independently a leaving group selected from a halogen, a labile hydrocarbyl, a substituted hydrocarbyl, a heteroatom group, or a divalent radical that links to an $R^2$, $R^3$, or $R^7$ group.

Another exemplary embodiment provides a catalyst composition comprising a catalyst compound supported to form a supported catalyst system, wherein the catalyst compound includes:

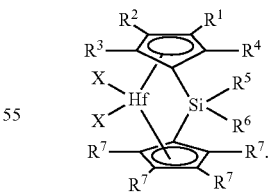

In this formula, $R^1$ is a saturated hydrocarbyl group of at least two carbons in length. $R^2$ is an H, a hydrocarbyl group, a substituted hydrocarbyl group, a heteroatom group, or connects to $R^3$ through a ring structure. $R^3$ is an H, a hydrocarbyl group, a substituted hydrocarbyl group, a heteroatom group, or connects to $R^2$ through a ring structure. $R^4$ is an H or a methyl group. $R^5$ is an H, a hydrocarbyl group, a substituted hydrocarbyl group, a heteroatom group, or forms a ring structure with $R^6$. $R^6$ is an H, a hydrocarbyl group, a substituted hydrocarbyl group, a heteroatom group, or forms a ring structure with $R^5$. Each $R^7$ is independently an H, a hydrocarbyl group, a substituted hydrocarbyl group, a heteroatom group, or connects to an adjacent $R^7$ group through a ring structure. Each X is independently a leaving group selected from a halogen, a labile hydrocarbyl, a substituted hydrocarbyl, a heteroatom group, or a divalent radical that links to an $R^2$, $R^3$, or $R^7$ group.

Another embodiment provides a polymer formed from a catalyst compound supported to form a supported catalyst system, wherein the catalyst compound includes:

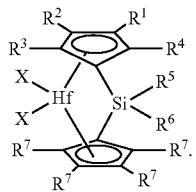

In this formula, $R^1$ is a saturated hydrocarbyl group of at least two carbons in length. $R^2$ is an H, a hydrocarbyl group, a substituted hydrocarbyl group, a heteroatom group, or connects to $R^3$ through a ring structure. $R^3$ is an H, a hydrocarbyl group, a substituted hydrocarbyl group, a heteroatom group, or connects to $R^2$ through a ring structure. $R^4$ is an H or a methyl group. $R^5$ is an H, a hydrocarbyl group, a substituted hydrocarbyl group, a heteroatom group, or forms a ring structure with $R^6$. $R^6$ is an H, a hydrocarbyl group, a substituted hydrocarbyl group, a heteroatom group, or forms a ring structure with $R^5$. Each $R^7$ is independently an H, a hydrocarbyl group, a substituted hydrocarbyl group, a heteroatom group, or connects to an adjacent $R^7$ group through a ring structure. Each X is independently a leaving group selected from a halogen, a labile hydrocarbyl, a substituted hydrocarbyl, a heteroatom group, or a divalent radical that links to an $R^2$, $R^3$, or $R^7$ group.

DETAILED DESCRIPTION

DETAILED DESCRIPTION

Figure 1:
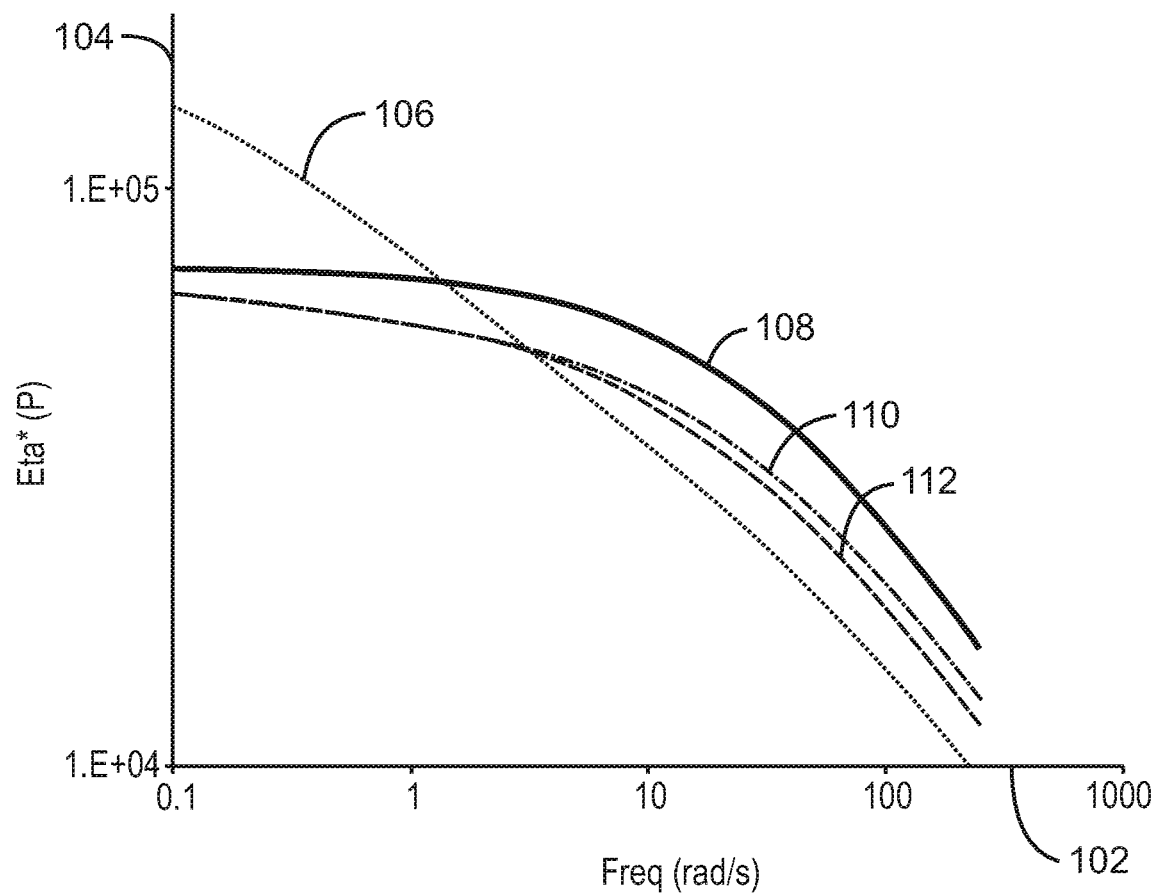
FIG. 1 is a graph of shear viscosity for polymers produced by the test catalysts versus the control polymers.

It has been discovered that bridged hafnocenes having a 3-propyl substituent are highly active on supports and appear to produce linear low density polyethylene with low or undetectable long chain branching. In addition, the comonomer (C6) incorporation is flat to slightly favoring a broad orthogonal composition distribution (BOCD). These properties provide attractive properties for films produced with this resin.

In lab testing an exemplary hafnocene ($Me_2Si(3$-n-propyl-$\eta^5$-Cp)($\eta^5$-$CpMe_4$)$HfMe_2$) (catalyst A) was supported on SMAO and run in a gas phase batch reactor, producing linear low density polyethylene (LLDPE) with activity of about 8000 g/g. Tests using cross fractionation chromatography (CFC) graph indicated a substantially flat comonomer distribution.

Rheology data for polymer produced with catalyst A was compared to a control polymer, Exceed® 1018 from ExxonMobil®, which is a commercial LLDPE resin. The data on the lab scale resins indicated that the polymer has no LCB which has been shown to deteriorate both toughness (dart) and tear properties in blown films.

Similar hafnocenes were expected to produce similar resins. To test this, catalyst A was used to produce a larger amount of resin at a pilot plant scale. Further, another catalyst, [(2-Me-3-n-Pr-$\eta^5$-Indenyl)-$SiMe_2$-($\eta^5$-$CpMe_4$)]$HfMe_2$, hereinafter "catalyst B", was also used to produce resin at the pilot plant scale. As discussed in the examples below, the resins produced by these catalysts were processed into blown film. The measured properties indicated that both catalysts produced resins with low long chain branching (LCB).

It is believed that a significant amount of the control over the LCB may be achieved, for example, by the n-alkyl substituent. Manipulation of the other ligands and bridges would allow for control of MW, commoner incorporation and activity. This may be achieved by a catalyst having the general structure shown in formula (I).

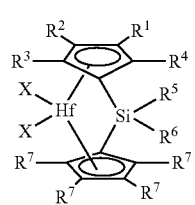

(I)

In formula (I), $R^1$ is a saturated hydrocarbyl group of at least two carbons in length. $R^2$ is an H, a hydrocarbyl group, a substituted hydrocarbyl group, a heteroatom group, or connects to $R^3$ through a ring structure. $R^3$ is an H, a hydrocarbyl group, a substituted hydrocarbyl group, a heteroatom group, or connects to $R^2$ through a ring structure. $R^4$ is an H or a methyl group. $R^5$ is an H, a hydrocarbyl group, a substituted hydrocarbyl group, a heteroatom group, or forms a ring structure with $R^6$. $R^6$ is an H, a hydrocarbyl group, a substituted hydrocarbyl group, a heteroatom group, or forms a ring structure with $R^5$. Each $R^7$ is independently an H, a hydrocarbyl group, a substituted hydrocarbyl group, a heteroatom group, or connects to an adjacent $R^7$ group through a ring structure. Each X is independently a leaving group selected from a halogen, a labile hydrocarbyl, a substituted hydrocarbyl, a heteroatom group, or a divalent radical that links to an $R^2$, $R^3$, or $R^7$ group. These catalysts can be used in single catalyst systems, or in cocatalyst systems using other metallocenes or catalysts, as discussed below.

Catalyst Compounds

Metallocene Catalyst Compounds

Metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving groups bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring systems, at least a portion of which includes π-bonded systems, such as cycloalkadienyl ligands and heterocyclic analogues. The rings or ring systems typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligands are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$ Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one exemplary embodiment; and selected from the group consisting of Groups 3 through 10 atoms in a more particular exemplary embodiment, and selected from the group consisting of Sc, Ti, Zr, Hf, V, Nb, Ta, Mn, Re, Fe, Ru, Os, Co, Rh, Ir, and Ni in yet a more particular exemplary embodiment; and selected from the group consisting of Groups 4, 5, and 6 atoms in yet a more particular exemplary embodiment, and Ti, Zr, Hf atoms in yet a more particular exemplary embodiment, and Hf in yet a more particular exemplary embodiment. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the formula (I):

$$Cp^A Cp^B M x_n \qquad (I)$$

in which M is as described above; each X is chemically bonded to M; each Cp group is chemically bonded to M; and n is 0 or an integer from 1 to 4, and either 1 or 2 in a particular exemplary embodiment.

The ligands represented by Cp$^A$ and Cp$^B$ in formula (I) can be the same or different cyclopentadienyl ligands or ligands isolobal to cyclopentadienyl, either or both of which can contain heteroatoms and either or both of which can be substituted by a group R. In at least one specific embodiment, Cp$^A$ and Cp$^B$ are independently selected from the group consisting of cyclopentadienyl, indenyl, tetrahydroindenyl, fluorenyl, and substituted derivatives of each.

Independently, each Cp$^A$ and Cp$^B$ of formula (I) can be unsubstituted or substituted with any one or combination of substituent groups R. Non-limiting examples of substituent groups R as used in structure (I) as well as ring substituents in structures Va-d, discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof. More particular non-limiting examples of alkyl substituents R associated with formulas (I) through (Va-d) include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like. Other possible radicals include substituted alkyls and aryls such as, for example, fluoromethyl, fluroethyl, difluroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide, and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each X in the formula (I) above and for the formulas, or structures, (II) through (Va-d) below is independently selected from the group consisting of: any leaving group, in one exemplary embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_8$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, in a more particular exemplary embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls, in yet a more particular exemplary embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls, in yet a more particular exemplary embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment; and fluoride, in yet a more particular exemplary embodiment.

Other non-limiting examples of X groups include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more Xs form a part of a fused ring or ring system. In at least one specific embodiment, X can be a leaving group selected from the group consisting of chloride ions, bromide ions, $C_1$ to $C_{10}$ alkyls, and $C_2$ to $C_{12}$ alkenyls, carboxylates, acetylacetonates, and alkoxides.

The metallocene catalyst compound includes those of formula (I) where $Cp^A$ and $Cp^B$ are bridged to each other by at least one bridging group, (A), such that the structure is represented by formula (II):

$$Cp^A(A)Cp^BMX_n \qquad (II)$$

These bridged compounds represented by formula (II) are known as "bridged metallocenes." The elements $Cp^A$, $Cp^B$, M, X and n in formula (II) are as defined above for formula (I); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be $C_1$ to $C_{12}$ alkyl or aryl substituted to satisfy neutral valency. In at least one specific embodiment, the bridging group (A) can also include substituent groups R as defined above (for formula (I)) including halogen radicals and iron. In at least one specific embodiment, the bridging group (A) can be represented by $C_1$ to $C_6$ alkylenes, substituted $C_1$ to $C_6$ alkylenes, oxygen, sulfur, $R'_2C=$, $R'_2Si=$, $=Si(R')_2Si(R'_2)=$, $R'_2Ge=$, and $R'P=$, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of formula (II) includes two or more bridging groups (A). In one or more embodiments, (A) can be a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties where the Si atom is replaced by a Ge or a C atom; as well as dimethylsilyl, diethylsilyl, dimethylgermyl and diethylgermyl.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, Cl). The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands $Cp^A$ and $Cp^B$ of formula (I) and (II) can be different from each other. The ligands $Cp^A$ and $Cp^B$ of formula (I) and (II) can be the same. The metallocene catalyst compound can include bridged mono-ligand metallocene compounds (e.g., mono cyclopentadienyl catalyst components).

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

The amount of the transition metal component of the one or more metallocene catalyst compounds in the catalyst system can range from a low of about 0.2 wt. %, about 3 wt. %, about 0.5 wt. %, or about 0.7 wt. % to a high of about 1 wt. %, about 2 wt. %, about 2.5 wt. %, about 3 wt. %, about 3.5 wt. %, or about 4 wt. %, based on the total weight of the catalyst system.

Other metallocene catalyst compounds that may be used are supported constrained geometry catalysts (sCGC) that include (a) an ionic complex, (b) a transition metal compound, (c) an organometal compound, and (d) a support material. In some embodiments, the sCGC catalyst may include a borate ion. The borate anion is represented by the formula $[BQ_{4-z}(G_q(T-H)_r)_{z'}]^{d-}$, wherein: B is boron in a valence state of 3; Q is selected from the group consisting of hydride, dihydrocarbylamido, halide, hydrocarbyloxide, hydrocarbyl, and substituted-hydrocarbyl radicals; z' is an integer in a range from 1 to 4; G is a polyvalent hydrocarbon radical having r+1 valencies bonded to M' and r groups (T-H); q is an integer, 0 or 1; the group (T-H) is a radical wherein T includes O, S, NR, or PR, the O, S, N or P atom of which is bonded to hydrogen atom H, wherein R is a hydrocarbyl radical, a trihydrocarbylsilyl radical, a trihydrocarbyl germyl radical or hydrogen; r is an integer from 1 to 3; and d is 1. Alternatively the borate ion may be representative by the formula $[BQ_{4-z}(G_q(T-M^oR^C_{x-1}X^a_y)_r)_{z'}]^{d-}$, wherein: B is boron in a valence state of 3; Q is selected from the group consisting of hydride, dihydrocarbylamido, halide, hydrocarbyloxide, hydrocarbyl, and substituted-hydrocarbyl radicals; z' is an integer in a range from 1 to 4; G is a polyvalent hydrocarbon radical having r+1 valencies bonded to B and r groups $(T-M^oR^C_{x-1}X^a_y)$; q is an integer, 0 or 1; the group $(T-M^oR^C_{x-1}X^a_y)$ is a radical wherein T includes O, S, NR, or PR, the O, S, N or P atom of which is bonded to $M^o$, wherein R is a hydrocarbyl radical, a trihydrocarbylsilyl radical, a trihydrocarbyl germyl radical or hydrogen; $M^o$ is a metal or metalloid selected from Groups 1-14 of the Periodic Table of the Elements, $R^C$ independently each occurrence is hydrogen or a group having from 1 to 80 nonhydrogen atoms which is hydrocarbyl, hydrocarbylsilyl, or hydrocarbylsilylhydrocarbyl; $X^a$ is a noninterfering group having from 1 to 100 nonhydrogen atoms which is halo-substituted hydrocarbyl, hydrocarbylamino-substituted hydrocarbyl, hydrocarbyloxy-substituted hydrocarbyl, hydrocarbylamino, di(hydrocarbyl)amino, hydrocarbyloxy or halide; x is a nonzero integer which may range from 1 to an integer equal to the valence of $M^o$; y is zero or a nonzero integer which may range from 1 to an integer equal to 1 less than the valence of $M^o$; and x+y equals the valence of $M^o$; r is an integer from 1 to 3; and d is 1. In some embodiments, the borate ion may be of the above described formulas where z' is 1 or 2, q is 1, and r is 1.

The catalyst system can include other single site catalysts such as Group 15-containing catalysts. The catalyst system can include one or more second catalysts in addition to the single site catalyst compound such as chromium-based catalysts, Ziegler-Natta catalysts, one or more additional single-site catalysts such as metallocenes or Group 15-containing catalysts, bimetallic catalysts, and mixed catalysts. The catalyst system can also include $AlCl_3$, cobalt, iron, palladium, or any combination thereof.

The metallocene catalyst compound can include any catalyst or combinations of catalysts discussed and described herein. For example, the metallocene catalyst compound can include, but is not limited to, $Me_2Si(3-n-propyl-\eta^5-Cp)(\eta^5-CpMe_4)HfMe_2$ (catalyst A), $[(2-Me-3-n-propyl-\eta^5-Indenyl)-SiMe_2-(\eta^5-CpMe_4)]HfMe_2$ (catalyst B), or any other catalyst compounds mentioned herein. The structural formula for these catalysts is:

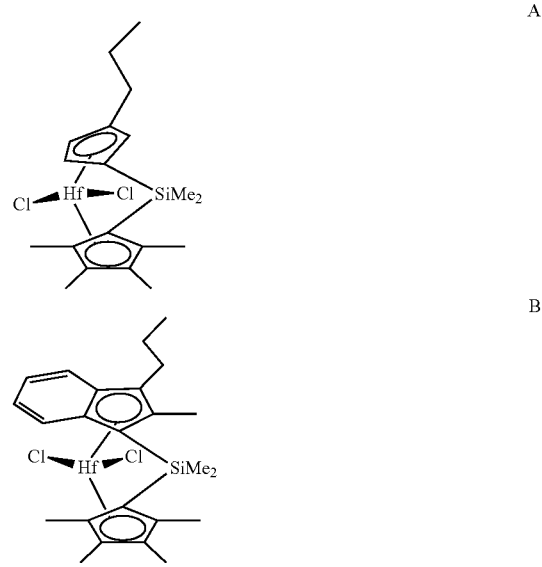

Catalyst Slurry

The catalyst system may include a catalyst or catalyst component in a slurry, which may have a single catalyst compound, or may have added catalyst components that are added as a solution to the slurry or cosupported on the support. Any number of combinations of catalyst components may be used in embodiments. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one or more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and a catalyst compound. In another embodiment the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator, such as aluminum, or metalloid, such as boron, to metal in the catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

Catalyst Supports

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand. The single site catalyst compounds of the slurry can be spray dried. The support used with the single site catalyst compound can be functionalized.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include alumina, silica, or a combination thereof. In one embodiment described herein, the support is silica.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalysts supports comprising silica gels with activators, such as methylaluminoxanes (MAOs), are used in the trim systems described, since these supports may function better for co-supporting solution carried catalysts. Suitable supports may also be selected from the Cab-o-sil® materials available from Cabot Corporation and silica materials available from the Grace division of W.R. Grace & Company.

Catalyst supports may also include polymers that are covalently bonded to a ligand on the catalyst. For example, two or more catalyst molecules may be bonded to a single polyolefin chain.

Catalyst Activators

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound or component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as Dimethylanilinium tetrakis(pentafluorophenyl)borate, Triphenylcarbenium tetrakis(pentafluorophenyl)borate, Dimethylanilinium tetrakis(3,5-$(CF_3)_2$phenyl)borate, Triphenylcarbenium tetrakis(3,5-$(CF_3)_2$phenyl)borate, Dimethylanilinium tetrakis(perfluoronapthyl)borate, Triphenylcarbenium tetrakis(perfluoronapthyl)borate, Dimethylanilinium tetrakis(pentafluorophenyl)aluminate, Triphenylcarbenium tetrakis(pentafluorophenyl)aluminate, Dimethylanilinium tetrakis(perfluoronapthyl)aluminate, Triphenylcarbenium tetrakis(perfluoronapthyl)aluminate, a tris(perfluorophenyl) boron, a tris(perfluoronaphthyl)boron, tris(perfluorophenyl) aluminum, a tris(perfluoronaphthyl)aluminum or any combinations thereof.

It is recognized that these activators may bind directly to the support surface or be modified to allow them to be bound to a support surface while still maintaining their compatability with the polymerization system. Such tethering agents may be derived from groups that are reactive with surface hydroxyl species. Non-limiting examples of reactive functional groups that can be used to create tethers include aluminum halides, aluminum hydrides, aluminum alkyls, aluminum aryls, sluminum alkoxides, electrophilic silicon reagents, alkoxy silanes, amino silanes, boranes.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes.

In one or more embodiments, a visually clear MAO can be used. For example, a cloudy or gelled aluminoxane can be filtered to produce a clear aluminoxane or clear aluminoxane can be decanted from a cloudy aluminoxane solution. In another embodiment, a cloudy and/or gelled aluminoxane can be used. Another aluminoxane can include a modified methyl aluminoxane ("MMAO") type 3A (commercially available from Akzo Chemicals, Inc. under the trade name Modified Methylaluminoxane type 3A, discussed and described in U.S. Pat. No. 5,041,584). A suitable source of MAO can be a solution having from about 1 wt. % to about a 50 wt. % MAO, for example. Commercially available MAO solutions can include the 10 wt. % and 30 wt. % MAO solutions available from Albemarle Corporation, of Baton Rouge, La.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Continuity Additive/Static Control Agents

In gas-phase polyethylene production processes, as disclosed herein, it may be desirable to additionally use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents, as well as those described in, for example, WO 01/44322, listed under the heading Carboxylate Metal Salt and including those chemicals and compositions listed as antistatic agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

—(CH$_2$—CH$_2$—NH)$_n$— in which n may be from about 10 to about 10,000. The polyethyleneimines may be linear, branched, or hyper-branched (e.g., forming dendritic or arborescent polymer structures). They can be a homopolymer or copolymer of ethyleneimine or mixtures thereof (referred to as polyethyleneimine(s) hereafter). Although linear polymers represented by the chemical formula —[CH$_2$—CH$_2$—NH]— may be used as the polyethyleneimine, materials having primary, secondary, and tertiary branches can also be used. Commercial polyethyleneimine can be a compound having branches of the ethyleneimine polymer. Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF. Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %.

The continuity additive(s) or static control agent(s) may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Controlling Product Properties

The properties of the product polymer may be controlled by adjusting the timing, temperature, concentrations, and sequence of the mixing of the solution, the slurry and any optional added materials (nucleating agents, catalyst compounds, activators, etc) described above. The MWD, composition distribution, melt index, relative amount of polymer produced by each catalyst, and other properties of the polymer produced may also be changed by manipulating process parameters. Any number of process parameters may be adjusted, including manipulating hydrogen concentration in the polymerization system, changing the amount of a catalyst in the polymerization system, changing the amount of a second catalyst in the polymerization system. Other process parameters that can be adjusted include changing the relative ratio of the catalyst in the polymerization process, and optionally adjusting their individual feed rates to maintain a steady or constant resin production rate. The concentrations of reactants in the reactor can be adjusted by changing the amount of liquid or gas that is withdrawn or purged from the process, changing the amount and/or composition of a recovered liquid and/or recovered gas returned to the polymerization process, wherein the recovered liquid or recovered gas can be recovered from polymer discharged from the polymerization process. Further concentration parameters that can be adjusted include changing the polymerization temperature, changing the ethylene partial pressure in the polymerization process, changing the ethylene to comonomer ratio in the polymerization process, changing the activator to transition metal ratio in the activation sequence. Time dependant parameters may be adjusted, such as changing the relative feed rates of the slurry or solution, changing the mixing time, the temperature and or degree of mixing of the slurry and the solution in-line, adding different types of activator compounds to the polymerization process, and adding oxygen or fluorobenzene or other catalyst poison to the polymerization process. Any combinations of these adjustments may be used to control the properties of the final polymer product.

In one embodiment, the composition distribution of the polymer product is measured at regular intervals and one of the above process parameters, such as temperature, catalyst compound feed rate, the ratio of comonomer to monomer, the monomer partial pressure, and or hydrogen concentration, is altered to bring the composition to the desired level, if necessary. The composition distribution may be performed by temperature rising elution fractionation (TREF), or similar techniques TREF measures composition as a function of elution temperature.

Polymerization Process

The catalyst system can be used to polymerize one or more olefins to provide one or more polymer products therefrom. Any suitable polymerization process can be used, including, but not limited to, high pressure, solution, slurry, and/or gas phase polymerization processes.

The terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, at least 95 wt. % ethylene-derived units, or 100 wt. % ethylene-derived units. The polyethylene can, thus, be a homopolymer or a copolymer, including a terpolymer, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like. Additionally, small amounts of diene monomers, such as 1,7-octadiene may be added to the polymerization to adjust polymer properties.

The reactor temperature of a fluid bed in a gas phase polymerization process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Preferred reactor temperatures are between 70 and 95° C. More preferred reactor temperatures are between 75 and 90° C. Thus, the upper temperature limit in one embodiment is the melting temperature of the polyethylene copolymer produced in the reactor. However, higher temperatures may result in narrower MWDs, which can be improved by the addition of the MCN, or other, co-catalysts, as described herein.

Hydrogen gas can be used in olefin polymerization to control the final properties of the polyolefin. Using certain catalyst systems, increasing concentrations (partial pressures) of hydrogen can increase the flow index (FI) of the polyethylene copolymer generated. The flow index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired flow index of the final polyolefin resin. For example, the mole ratio of hydrogen to total monomer ($H_2$:monomer) can be greater than about 0.0001, greater than about 0.0005, or greater than about 0.001. Further, the mole ratio of hydrogen to total monomer ($H_2$:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm. Further, the ratio of hydrogen to total monomer ($H_2$:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

As noted, a slurry polymerization process can also be used in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. In one embodiment, a hexane, isopentane, or isobutane medium can be employed. The slurry can be circulated in a continuous loop system.

The product polyethylene can have a melt index ratio (MIR or $I_{21}/I_2$) ranging from about 5 to about 300, or from about 10 to less than about 150, or, in many embodiments, from about 15 to about 50. Flow index (FI, HLMI, or $I_{21}$ can be measured in accordance with ASTM D1238 (190° C., 21.6 kg). The melt index (MI, $I_2$) can be measured in accordance with ASTM D1238 (at 190° C., 2.16 kg weight).

Density can be determined in accordance with ASTM D-792. Density is expressed as grams per cubic centimeter (g/cm$^3$) unless otherwise noted. The polyethylene can have a density ranging from a low of about 0.89 g/cm$^3$, about 0.90 g/cm$^3$, or about 0.91 g/cm$^3$ to a high of about 0.95 g/cm$^3$, about 0.96 g/cm$^3$, or about 0.97 g/cm$^3$. The polyethylene can have a bulk density, measured in accordance with ASTM D1895 method B, of from about 0.25 g/cm$^3$ to about 0.5 g/cm$^3$. For example, the bulk density of the polyethylene can range from a low of about 0.30 g/cm$^3$, about 0.32 g/cm$^3$, or about 0.33 g/cm$^3$ to a high of about 0.40 g/cm$^3$, about 0.44 g/cm$^3$, or about 0.48 g/cm$^3$.

The polyethylene can be suitable for such articles as films, fibers, nonwoven and/or woven fabrics, extruded articles, and/or molded articles. Examples of films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or nonwoven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions in the form of bottles, tanks, large hollow articles, rigid food containers and toys, etc.

Examples

To provide a better understanding of the foregoing discussion, the following non-limiting examples are provided. All parts, proportions, and percentages are by weight unless otherwise indicated.

As described herein, comonomer, such as a $C_4$-$C_8$ alpha-olefin is added to a reaction, along with ethylene monomer, to create short chain branching (SCB) in polyethylene copolymers. Without intending to be being limited by theory, the SCB may cause a long PE chain to break free from a crystallite and be partly incorporated into other crystallites. Accordingly, polymers that have SCB on longer chains may exhibit higher toughness.

In contrast, long chain branching (LCB) are points at which two polymer chains may divide off from single polymer chains. As noted herein, LCB may enhance toughness, but cause the polymer to more vulnerable to orientation, causing lower tear strength in the direction of extrusion.

Control of Long Chain Branching from Hafnocene Catalysts

Two catalysts were tested for the determination of long chain branching from bridged systems. The catalysts have the structures shown below. The molecular weight of catalyst A is 534 g/mol, while the molecular weight of catalyst B is 598 g/mol.

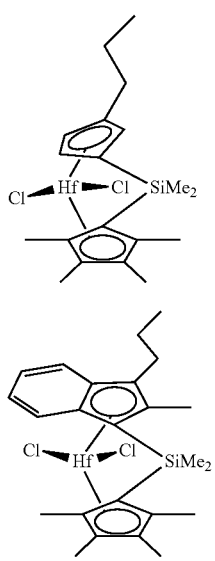

A

B

As described above, preliminary laboratory scale analysis of a resin produced in a gas phase batch reactor from catalyst A indicated no detectable levels of long chain branching (LCB) by melt strength (MS), gel permeation chromatography (GPC), and shear rheology. To further test whether these types of catalysts provided control over LCB, the initial hafnocene catalyst, A, and a related hafnocene catalyst, B, were scaled up and run in in 13.5 inch pilot plant reactor, as described in the experimental section below. Table 1 provides the reactor settings and test results for resins produced from the pilot plant run. The polymers made from catalysts A and B were stabilized with a commercial additive package and extruded using a 57 mm lab scale extruder prior to film extrusion.

For testing, films were blown from the resins produced on a 2.5 inch screw diameter blown film line from Gloucester Engineering (GEC) of Gloucester, Mass. The machine settings for the film blowing process of the 1 mil (25.4 µm) are shown in Table 2. Film was produced at two thicknesses, 1 mil (25.4 µm), and 2 mil (50.8 µm). The control extruded back to back with the test polymers was Exceed 1018, a commercial grade LLDPE produced by a metallocene catalyst that produces very little long chain branching. The parameters used for blowing a 1 mil film are shown in Table 2. In further studies, properties from a prior film extrusion run of a commercial resin, Enable 2010, was added as the 2nd control. The Enable 2010 was produced at similar conditions to the other resins except that the production rate was at 8 lbs/hr*inch die rather than the 10 lbs/hr*inch die used for the current resins. The Enable 2010 is also an LLDPE produced by a metallocene catalyst. However, Enable 2010 has significantly higher long chain branching.

FIG. 1 is a graph 100 of shear viscosity for polymers produced by the test catalysts versus the control polymers. The x-axis 102 is the frequency in radians/second, while the y-axis 104 is the viscosity (η) in poise (1 poise=100 millipascal second). As shown in the graph 100, the Exceed 1018 108 has the flattest curve, while Enable 2010 106 has nearly a uniform dropoff starting at a higher value for η at a low frequency. Enable 2010 curve is considered an indication of LCB, e.g., higher viscosity readings at lower frequencies. The polymers made from the test catalysts, catalyst B 110 and catalyst A 112, land between the controls, but closer in properties to the Exceed 1018 behavior, indicating low long chain branching.

Figure 2:
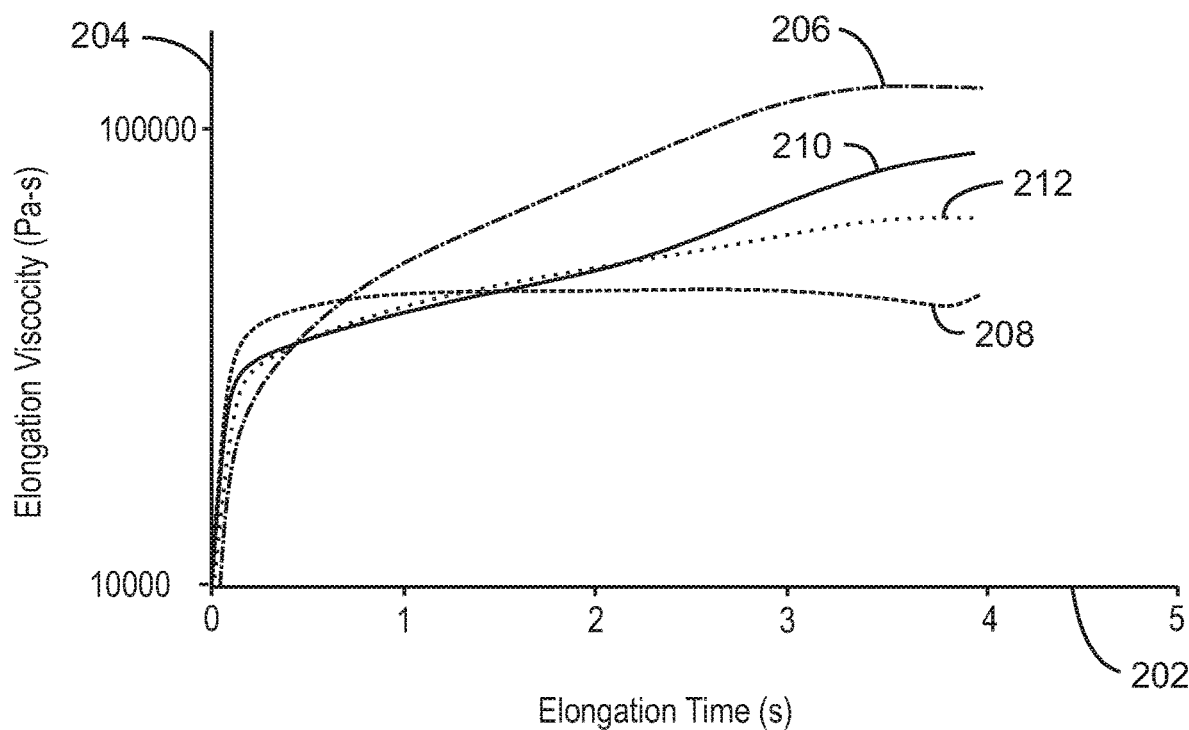
FIG. 2 is a graph of elongation viscosity for polymers produced by the test catalysts versus the control polymers.

FIG. 2 is a graph 200 of elongation viscosity for polymers produced by the test catalysts versus the control polymers. The x-axis 202 is the elongation time in seconds, while the y-axis 204 is the elongation viscosity in pascals second. This measurement highlights strain hardening, which may be an indication of long chain branching. The Enable 2010 206 has the highest values, indicating the highest long chain branching. In contrast, the Exceed 1018 has the lowest values and remains relatively flat over the entire time span, indicating minimal long chain branching. The test polymers land between the controls, with the polymer formed from catalyst B 210 closer to the Enable 2010 206 curve and the polymer formed from catalyst A 212 closer to the Exceed 1018 208 curve.

Figure 3:
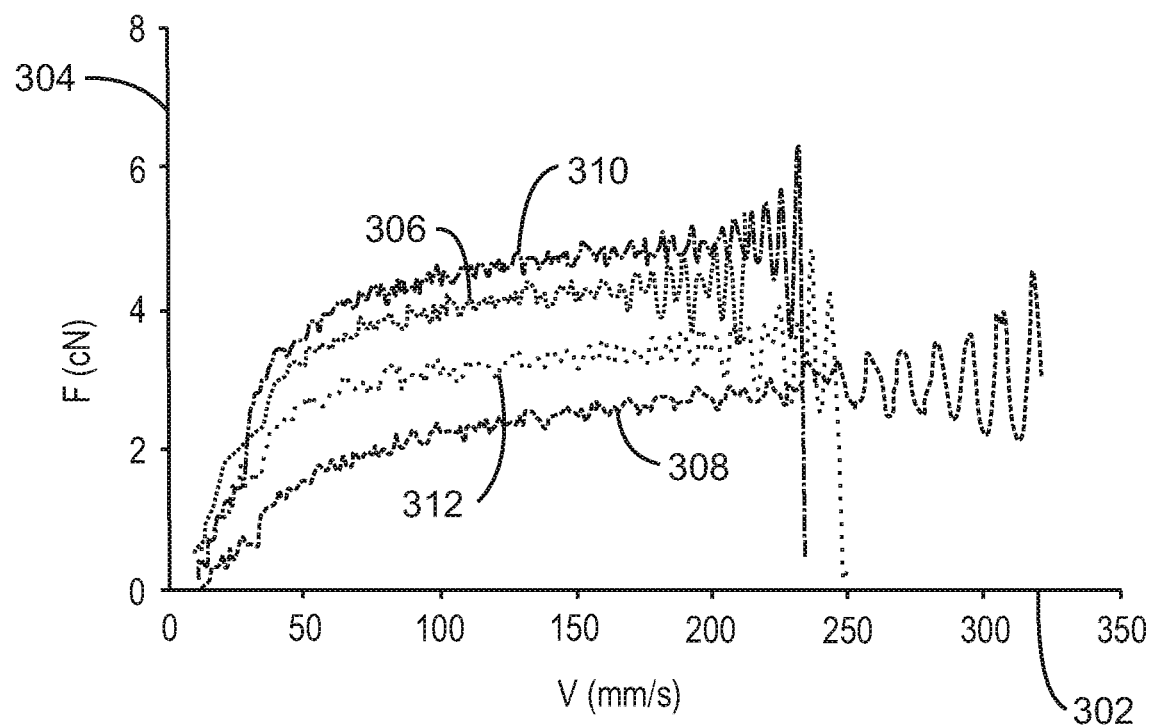
FIG. 3 is a graph of melt strength for polymers produced by the test catalysts versus the control polymers.
Figure 7:
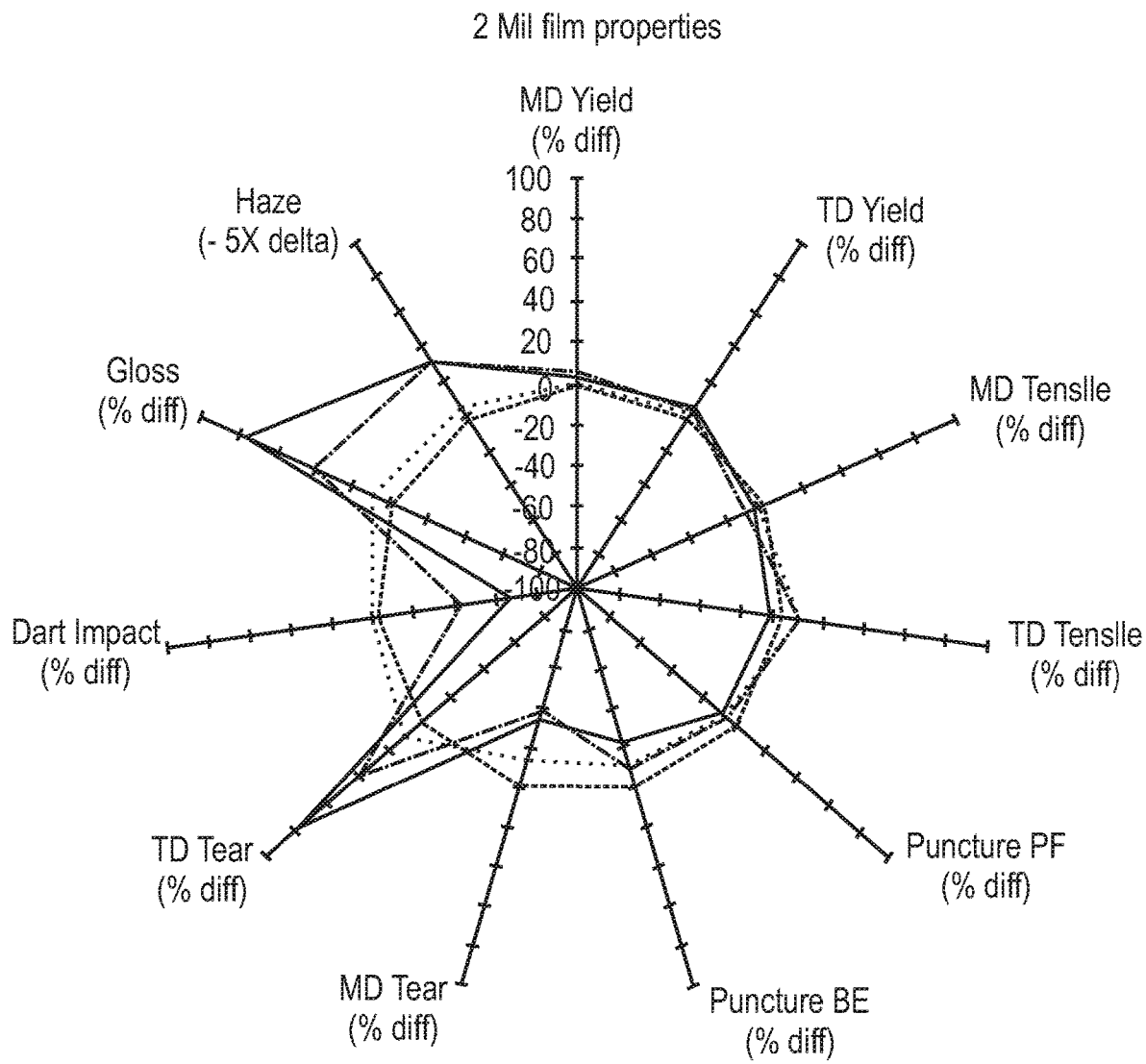
FIG. 7 is a comparative chart of physical properties for 2-mil (50.8 μm) films made from the test polymers and compared to an Enable resin, using Exceed as a control.

FIG. 3 is a graph 300 of melt strength for polymers produced by the test catalysts versus the control polymers. The x-axis 302 is the velocity in millimeters per seconds, while the y-axis 304 is the melt strength in force in centiNewtons. These plots also indicate differences due to strain hardening, such as the break point that is indicated by the termination of measure values along the x-axis 302. As shown in the graph 300, the Enable 2010 306 terminates first with a relatively high MS value, which is consistent with the level of long chain branching in the polymer. Similarly, the Exceed 1018 terminates farthest with a relatively low MS value, indicating low, or no, long chain branching. The test polymers landed between these values, with the polymer made from catalyst B 310 being close to the Enable 2010 306 and the polymer made from catalyst A 312 being close to Exceed 1018 308. The physical properties obtained from film testing also indicate the presence or absence of long chain branching. Further, the test results may show the benefits obtained by controlling the long chain branching. As noted, the test results for the films are shown in Tables 3 (1 mil films) and 5 (2 mil films). Comparative results, calculated as a percent differential from Exceed 1018 are shown in Tables 4 and 6. As a result of the calculation, the values for Exceed 1018 in the plots shown in FIGS. 4, 5, and 7 provide a baseline at zero.

Figure 4:
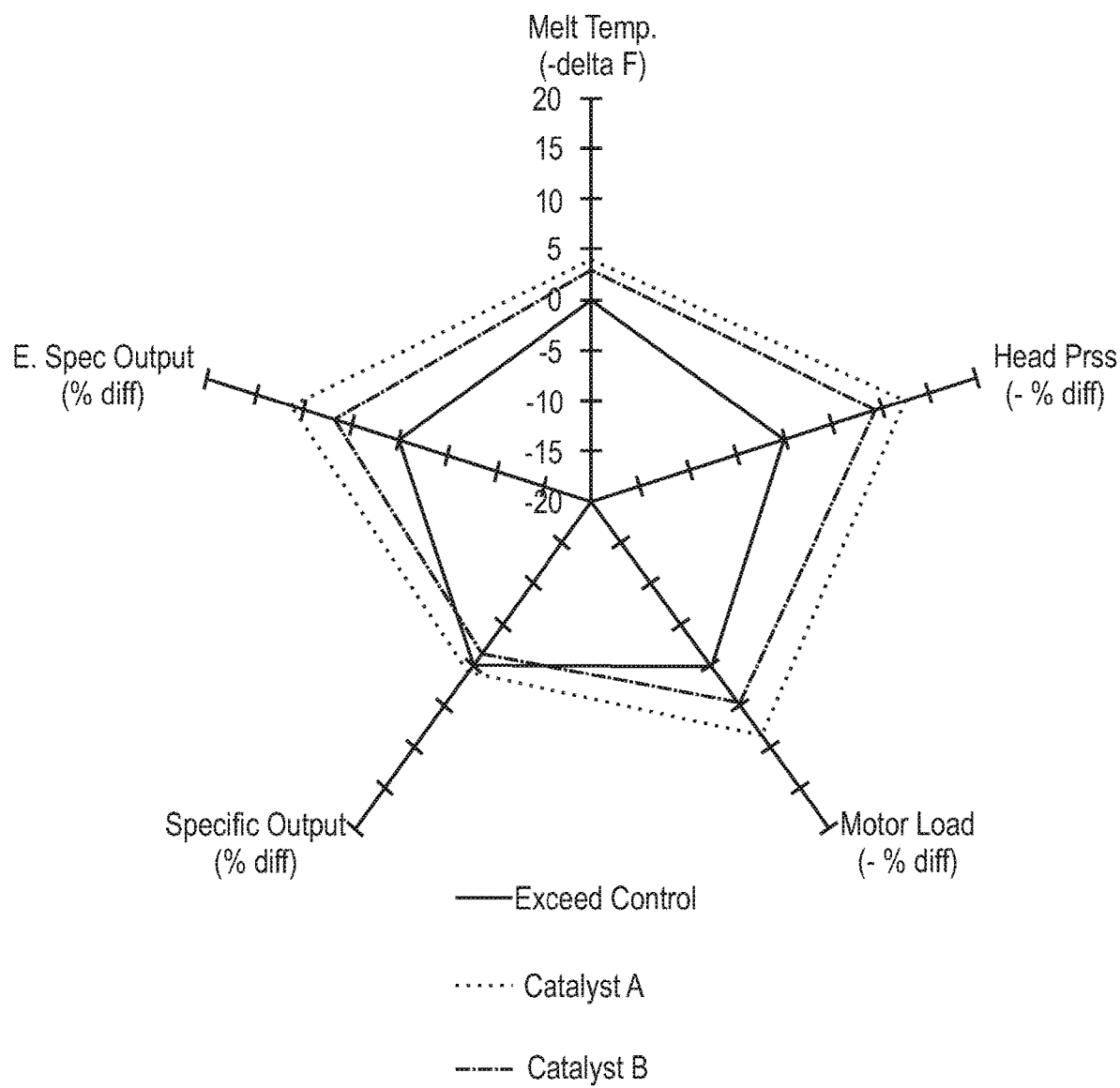
FIG. 4 is a comparative chart showing the values used to produce a 1 mil film of the two test polymers versus a control.

FIG. 4 is a comparative chart 400 showing the values used to produce a 1 mil film of the two test polymers versus a control. The output may be controlled by an operator, for example, at about 189 lbs/hr (86 kg/hr), allowing a comparison of the other values, such as specific output, Energy specific output, motor load and the like. The comparison may reflect the somewhat higher long chain branching in the test polymers versus the Exceed control, although molecular weight and molecular weight distribution may also play a role.

Figure 5:
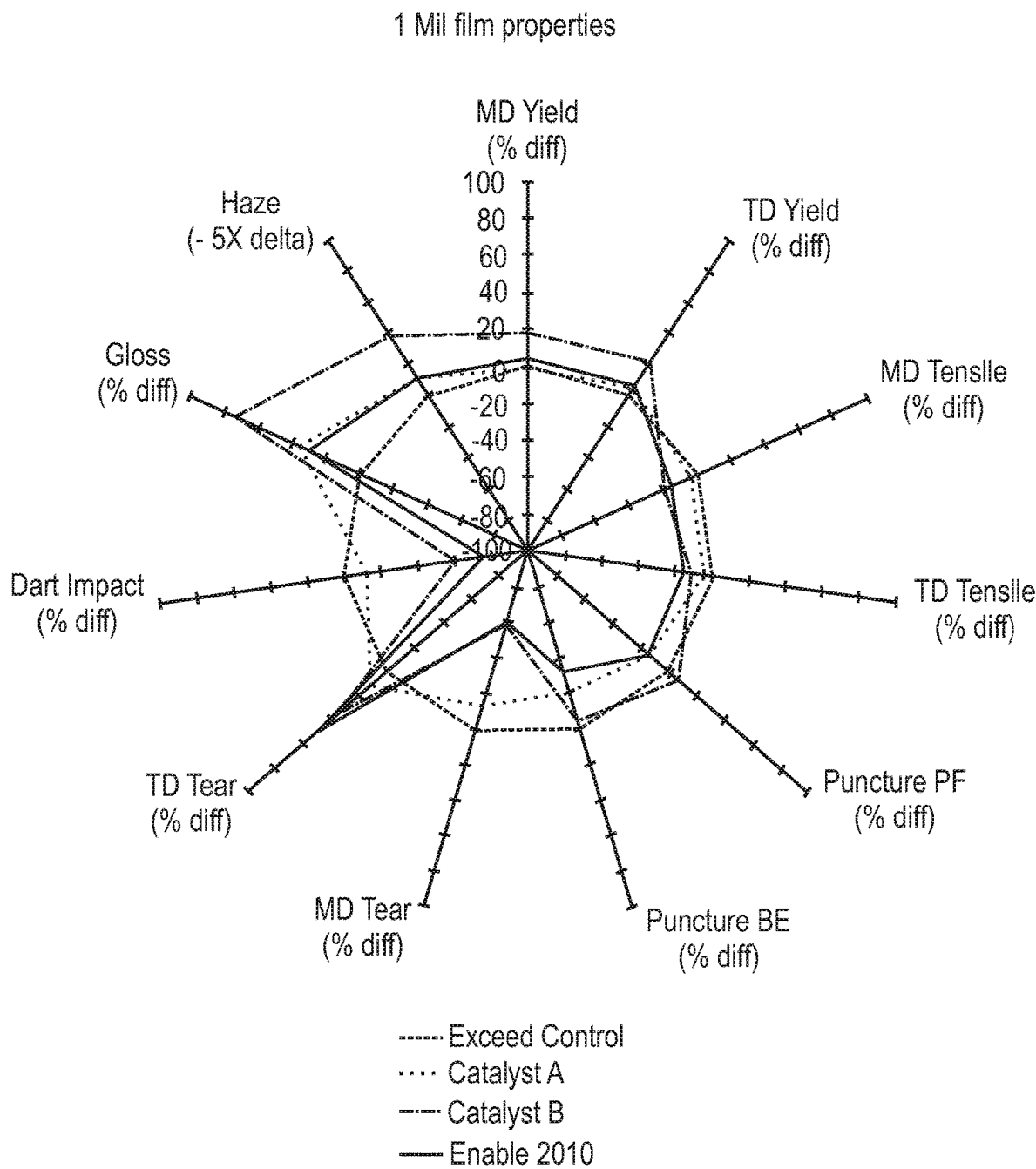
FIG. 5 is a comparative chart of physical properties for 1-mil (25.4 μm) films made from the test polymers and compared to an Enable resin using Exceed as a control.

FIG. 5 is a comparative chart 500 of physical properties for 1-mil (25.4 μm) films made from the test polymers and compared to an Enable resin using Exceed as a control. As control, the values for Exceed are also at zero in this chart 500. The differences in performance caused by long chain branching are most apparent in the anisotropy in the tear values. Long chain branching contributes to the alignment of polymer chains in the flow or machine direction, increasing the transverse direction (TD) tear strength and decreasing the machine direction (MD) tear. This is shown by the substantial anisotropy of the Enable resin versus the Exceed control. The polymer formed by test catalyst A gave values much closer to Exceed, while the polymer formed by catalyst B gave values much closer to those for Enable. As polymers formed from catalysts A and B have comparable MI and MIR, the anisotropy is believed to originate from the difference in LCB. Similarly, the dart impact strength of test polymers land between the values of the Exceed and Enable resins, with polymer formed from catalyst B being closer to Enable resin, indicating its degree of LCB is greater than that of the polymer formed from catalyst A.

Figure 6:
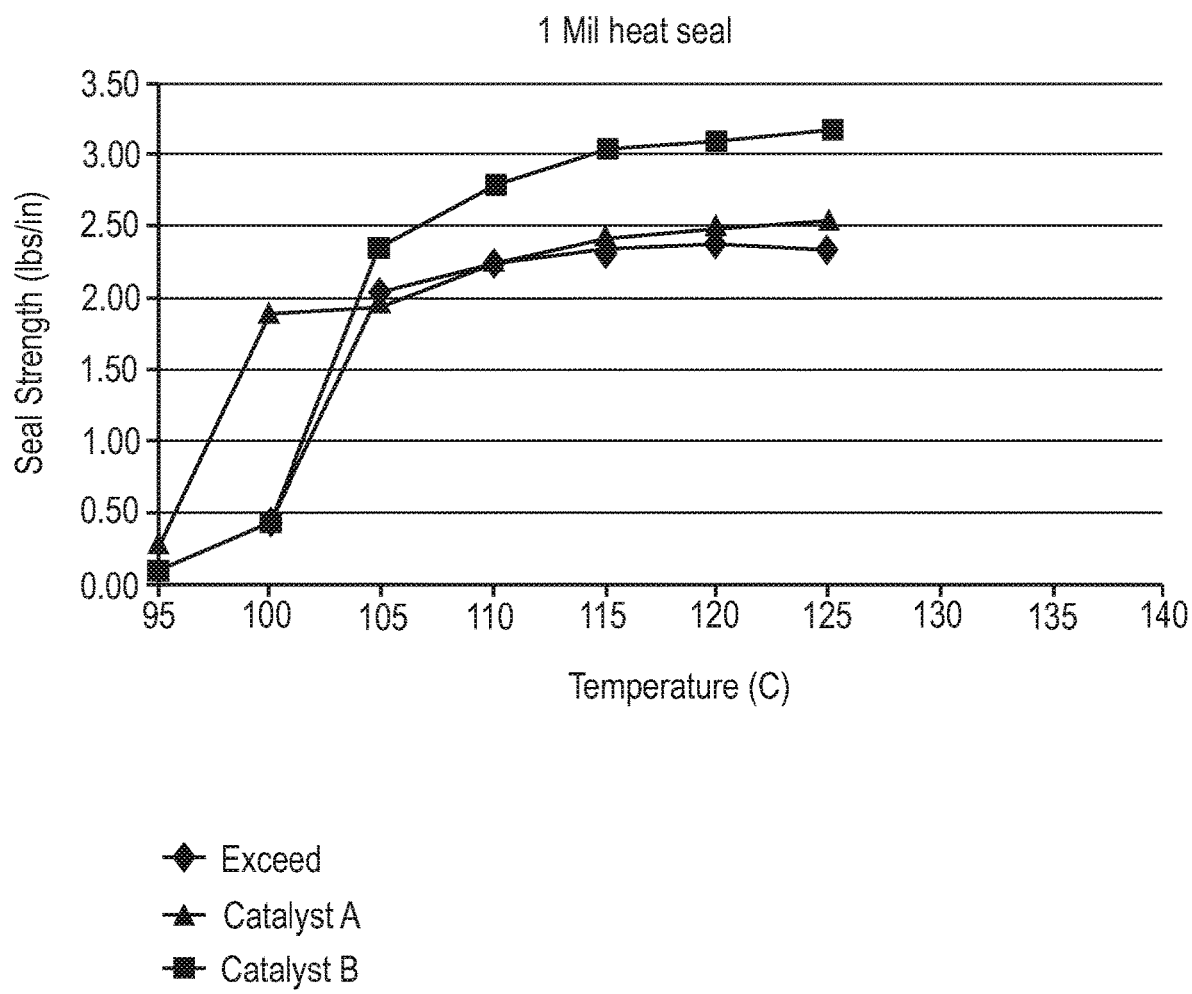
FIG. 6 is a graph showing that the polymers made by the test catalysts have heat seal properties similar to those of the Exceed control.

FIG. 6 is a graph showing that the polymers made by the test catalysts have heat seal properties similar to those of the Exceed control. In this case, the heat seal properties are dominated by density. The polymer formed from catalyst A has the lowest density.

Figure 8:
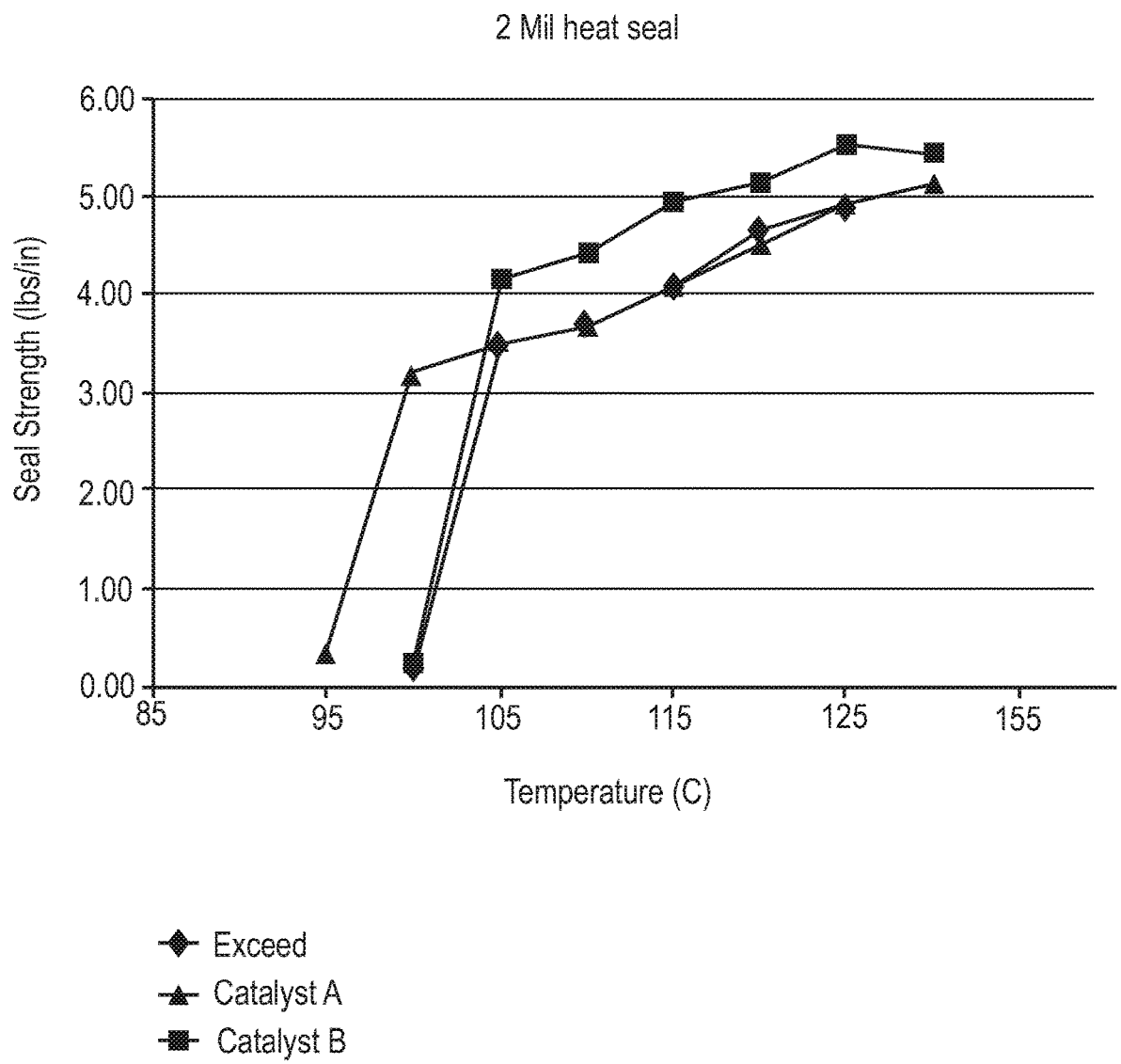
FIG. 8 is a graph showing that the polymers made by the test catalysts have heat seal properties similar to those of the Exceed control.

FIG. 7 is a comparative chart 700 of physical properties for 2-mil (50.8 μm) films made from the test polymers and compared to an Enable resin, using Exceed as a control. As control, the values for Exceed are also at zero in this chart 700. As for the 1-mil films, the differences in performance caused by long chain branching are most apparent in the anisotropy in the tear values. In this example, the polymer formed by test catalyst A again gave values close to Exceed. In 2-mil films, the anisotropy in the polymer was less significant, tear strength values obtained from polymer formed by catalyst B were still closer to those for the Enable control. Again, the dart impact strength of test polymers land between the values of the Exceed and Enable, with polymer formed from catalyst B being closer to Enable resin, indicating the its degree of LCB may be greater than that of the polymer formed from catalyst A. FIG. 8 is a graph 800 showing that the polymers made by the test catalysts have heat seal properties similar to those of the Exceed control. It can be noted that for both the 1-mil and 2-mil films, the polymer made from catalyst A had a lower heat sealing temperature than the Exceed resin. This may be due to a lower density for the polymers formed from catalyst A.

General Procedures for Forming Catalyst Components

Experimental

All manipulations were performed in an $N_2$ purged glovebox or using standard Schlenk techniques. All anhydrous solvents were purchased from Sigma-Aldrich and were degassed and dried over calcined $Al_2O_3$ beads or molecular sieves prior to use. Deuterated solvents were purchased from Cambridge Isotope Laboratories and were degassed and dried over alumina beads or molecular sieves prior to use. Reagents used were purchased from Sigma-Aldrich. $^1H$ NMR measurements were recorded on a 250 MHz, 400 MHz, or a 500 MHz Bruker spectrometer.

Catalyst Preparations

Synthesis of $Me_2Si(3\text{-Propyl-}\eta^5\text{-}C_5H_3)(\eta^5\text{-}Me_4C_5)$ $HfCl_2$ (Catalyst A)

$Me_2ClSi\text{-}Me_4C_5H$ (13.6 g) was dissolved in THF (200 ml) and reacted with $LiC_5H_4\text{—}C_3H_7$ (7.3 g) at room temperature for 15 hrs. The volatiles were removed in vacuo and the crude reaction mixture was extracted with hexane (2×50 ml). The extracts were filtered and reduced in vacuo (19.3 g). All was dissolved in $Et_2O$ (200 ml) and reacted with nBuLi (10.2 g 10 M). The reaction was stirred for 15 hrs and filtered to collect product. The white solid was washed with hexane (60 ml) and toluene (1×80 ml, 1×30 ml) and dried in vacuo (18.2 g). The dilithiated ligand was dissolved in $Et_2O$ (200 ml) and reacted with $HfCl_4$ (12.5 g). The reaction was stirred for 2 hrs and filtered through a PE frit. The residue was extracted with $Et_2O$ (2×40 ml) and $CH_2Cl_2$ (40 ml) and $Et_2O$ (100 ml). All filtrates were combined, reduced in volume and cooled to −30° C. The product was collected after 3 days as light yellow solid (7.8 g). A second crop was collected (1.1 g).

$^1H$ NMR (400 MHz, $CD_2Cl_2$) 8; 6.54 (m), 5.58 (m), 5.24 (m), 2.65 (m), 2.05 (s), 2.01 (s), 1.98 (s), 1.92 (s), 1.55 (m), 0.91 (t), 0.81 (s), 0.78 (s).

Synthesis of Supported Catalyst A

Methylalumoxane, MAO, (Albemarle, 1253 g of 10 wt % in toluene) and toluene (358 g) were mixed together at room temperature. A solution of catalyst A (11.5 g) in 100 ml of toluene was added to the MAO mixture and the crude mixture was stirred for 30 minutes. 343 g of silica (ES757, Ineos, dehydrated at 875° C.) was added to the reaction mixture and was stirred for 1 hr at room temperature. The volatiles were removed at 75° C. in vacuo until a free flowing solid was obtained (439 g).

Synthesis of $Me_2Si(2\text{-Me,3-Propyl-}\eta^5\text{-}C_9H_4)(\eta^5\text{-}Me_4C_5)HfCl_2$ (Catalyst B)

$2\text{-MeC}_9H_7$ (15 g) was dissolved in $Et_2O$ (240 ml) and reacted with nBuLi (9 g 10 M). After stirring for 1 hr the volatiles were removed in vacuo and the white solid remaining was slurried in hexane (240 ml) and collected on a frit and dried. The solid was slowly added to $C_3H_7Br$ (115 g) dissolved in $Et_2O$ (300 ml) and the reaction allowed to proceed for 15 hrs. The volatiles were removed and the residue extracted with hexane (2×80 ml). $Et_2O$ (100 ml) was added to the extracts and nBuLi (9 g 10 M) was added slowly. After 2 hrs the crude intermediate, 2-Me,3-$PropylC_9H_4Li$ (12.8 g) was isolated and washed with hexane (2×50 ml). $Me_2ClSi\text{-}Me_4C_5H$ (15.4 g) was dissolved in THF (200 ml) and reacted with 12.8 g of the 2-Me,3-PropylC$_9$H$_4$Li for 1 hr. The volatiles were removed and the crude Me$_2$Si(2-Me,3-PropylC$_9$H$_5$)(Me$_4$C$_5$H) filtered over 50 g silica gel (200-400 mesh) using 120 ml hexane as eluent. The volatiles were removed and the residue was dissolved in Et$_2$O (100 ml) and reacted with nBuLi (16 g 10 M) for 40 hrs. The volatiles were removed and the crude [Me$_2$Si(2-Me,3-PropylC$_9$H$_4$)(Me$_4$C$_5$)][Li$_2$] washed with hexane, slurried in Et$_2$O (150 ml) and reacted with HfCl$_4$ (17.5 g). After 2 hrs the crude product was collected by filtration and extracted with Et$_2$O (3×40 ml) and CH$_2$Cl$_2$ (2×30 ml). The combined filtrates were reduced to 40 ml and cooled to −30° C. A first crop (7.2 g) and a second crop (7.9 g) were collected.

$^1$H NMR (400 MHz, CD$_2$Cl$_2$) δ; 7.64 (m), 6.45 (m), 7.26 (m), 6.88 (m), 2.78 (m), 2.15 (s), 2.06 (s), 1.99 (s), 1.96 (s), 1.81 (s), 2.52 (m), 1.20 (s), 1.08 (s), 0.92 (t).

Synthesis of Supported Catalyst B

Methylalumoxane, MAO, (Albemarle, 1436 g of 10 wt % in toluene) and toluene (442 g) were mixed together at room temperature. A solution of catalyst B (14.8 g) in 100 ml of toluene was added to the MAO mixture and the crude mixture was stirred for 30 minutes. 392 g of silica (ES757, Ineos, dehydrated at 875° C.) was added to the reaction mixture and was stirred for 1 hr at room temperature. The volatiles were removed at 75° C. in vacuo until a free flowing solid was obtained (516 g).

Description of 13.25 Inch Diameter Gas-Phase Reactor

The polymerizations were conducted in a continuous gas phase fluidized bed reactor having a straight section of 13.25 inches (33.6 cm) diameter with a length of approximately 6.35 feet (1.94 m) and an expanded section of 12.58 feet (3.83 m) length and 2.43 feet (0.74 m) diameter at the largest width. The fluidized bed is made up of polymer granules. The gaseous feed streams of ethylene and hydrogen together with liquid 1-hexene were mixed together in a mixing tee arrangement and introduced below the reactor bed into the recycle gas line. The individual flow rates of ethylene, hydrogen and 1-hexene were controlled to maintain fixed composition targets. The ethylene concentration was controlled to maintain a constant ethylene partial pressure. The hydrogen and 1-hexene were controlled to maintain a constant hydrogen to ethylene mole ratio and a constant 1-hexene to ethylene mole ratio in the recirculating gas. The concentrations of all gasses were measured by an on-line gas chromatograph to ensure relatively constant composition in the recycle gas stream. The hydrogen was controlled to maintain constant hydrogen to ethylene mole ratio.

The reacting bed of growing polymer particles was maintained in a fluidized state by the continuous flow of the make-up feed and recycle gas through the reaction zone. A superficial gas velocity of 0.6-0.9 meters/sec was used to achieve this. The fluidized bed was maintained at a constant height by withdrawing a portion of the bed at a rate equal to the rate of formation of particulate product. The polymer production rate was in the range of 15-25 kg/hour. The product was removed semi-continuously via a series of valves into a fixed volume chamber. This product was purged to remove entrained hydrocarbons and treated with a small stream of humidified nitrogen to deactivate any trace quantities of residual catalyst.

The catalyst was fed as a dry solid. The feed rate of the catalyst was adjusted for overall polymer production rate, while also manipulating reaction temperature and the gas compositions in the reactor. The reactor was operated at a total pressure of about 350 psig (2413 kPa gauge). To maintain a constant fluidized bed temperature in the reactor, the temperature of the recycle gas was continuously adjusted up or down by passing the recirculating gas through the tubes of a shell-and-tube heat exchanger with cooling water on the shell-side to accommodate any changes in the rate of heat generation due to the polymerization.

A slurry mixture of anti-static agents in degassed and dried mineral oil (1:1 Aluminum stearate: N-nonyldiethanolamine at 20 wt % concentration) was fed into the reactor using a mixture of iso-pentane and nitrogen at such a rate as to achieve a concentration of between 38 and 123 ppmw anti-static agents in the fluidized bed. Isopentane and/or nitrogen was optionally employed to assist in conveying and dispersing the slurry mixture of anti-static into the reactor fluidized bed via a ⅛ inch to 3/16 inch OD injection tube extending a few inches into the bed from the reactor side wall.

Physical Testing Procedures

Shear viscosity data were obtained by using a Dynamic Shear Rheometer. The temperature used was 190° C., The sample preheat period was 5 mins. All samples were stabilized and extruded prior to tests.

Elongational Viscosity data were collected at 150° C. Multiple rates were used to characterize the polymers. Data obtained from 1 S$^{-1}$ were presented in this application. All samples werer stabilized and extruded prior to tests.

Melt Strength data were collected at 190 degree ° C. The acceleration was 2.4 mm/s$^2$ and the piston speed was 0.265 mm/s. All samples were stabilized and extruded prior to tests.

Tensile Strength and Modulus were performed on the samples conforming to ASTM D882. Tensile Strength and 1% secant Modulus were performed separately due to rate difference. All samples were conditioned by following ASTM D618 before testing Elemndorf Tear tests were performed conforming to ASTM D1922. All samples were conditioned by following ASTM D618 before testing.

Dart Drop was performed by following ASTM D 1709 method A. A Phenolic Dart head was used. All samples were conditioned by following ASTM D 618 before testing.

Haze was performed by following ASTM D1003. All samples were conditioned by following ASTM D 618 before testing.

Gloss was performed by following ASTM D2457. All samples were conditioned by following ASTM D618 before testing.

Cross-Fractionation Chromatography (CFC)

Cross-fractionation chromatography (CFC) was performed on a CFC-2 instrument from Polymer Char, Valencia, Spain. The instrument was operated and subsequent data processing, e.g., smoothing parameters, setting baselines, and defining integration limits, was performed according to the manner described in the CFC User Manual provided with the instrument or in a manner commonly used in the art. The instrument was equipped with a TREF column (stainless steel; o.d., ⅜"; length, 15 cm; packing, non-porous stainless steel micro-balls) in the first dimension and a GPC column set (3×PLgel 10 μm Mixed B column from Polymer Labs, UK) in the second dimension. Downstream from the GPC column was an infrared detector (IR4 from Polymer Char) capable of generating an absorbance signal that is proportional to the concentration of polymer in solution.

The sample to be analyzed was dissolved in ortho-dichlorobenzene, at a concentration of about 5 mg/ml, by stirring at 150° C. for 75 min. Then a 0.5-ml volume of the solution containing 2.5 mg of polymer was loaded in the center of the TREF column and the column temperature was reduced and stabilized at ≈120° C. for 30 min. The column was then cooled slowly (0.2° C./min) to 30° C. (for ambient runs) or −15° C. (for cryogenic runs) to crystallize the polymer on the inert support. The low temperature was held for 10 min before injecting the soluble fraction into the GPC column. All GPC analyses were done using solvent ortho-dichlorobenzene at 1 ml/min, a column temperature of 140° C., and in the "Overlap GPC Injections" mode. Then the subsequent higher-temperature fractions were analyzed by increasing the TREF column temperature to the fraction set-points in a stepwise manner, letting the polymer dissolve for 16 min ("Analysis Time"), and injecting the dissolved polymer into the GPC column for 3 min ("Elution Time").

The universal calibration method was used for determining the molecular mass of eluting polymers. Thirteen narrow molecular-weight distribution polystyrene standards (obtained from Polymer Labs, UK) within the range of 1.5-8200 Kg/mol were used to generate a universal calibration curve. Mark-Houwink parameters were obtained from Appendix I of "Size Exclusion Chromatography" by S. Mori and H. G. Barth (Springer). For polystyrene $K=1.38\times10^{-4}$ dl/g and $\alpha=0.7$; and for polyethylene $K=5.05\times10-4$ dl/g and $\alpha=0.693$ were used. Fractions having a weight % recovery (as reported by the instrument software) of less than 0.5% were not processed for calculations of molecular-weight averages ($M_n$, $M_w$, etc.) of the individual fractions or of aggregates of fractions.

TABLE 1

Reactor settings and test results from pilot plant run

| Cat | Part BTO | REACTOR BED TEM DEG ° C./C | C6/C2 RATIO mol ratio | H2 PPM | AI Activity XRF | LAB EXT MI(I2) | MFR I21/12 Extruded | LAB EXT DENS |
|---|---|---|---|---|---|---|---|---|
| EXCEED 1018 | 5.28 | 85.0 | 0.02160 | 140.5 | | 0.903 | 16.385 | 0.9172 |
| EXCEED 1018 | 6.31 | 85.0 | 0.02106 | 144.6 | 7834 | 0.954 | 16.160 | 0.9178 |
| EXCEED 1018 | 7.33 | 85.0 | 0.02100 | 146.8 | | 0.951 | 16.212 | 0.9180 |
| EXCEED 1018 | 8.36 | 85.0 | 0.02101 | 146.7 | 5353 | 0.945 | 15.670 | 0.9178 |
| catalyst A | 5.02 | 79.0 | 0.01439 | 368.0 | 6856 | 1.064 | 22.502 | 0.9162 |
| catalyst A | 5.94 | 79.0 | 0.01429 | 361.3 | | 1.060 | 22.188 | 0.9166 |
| catalyst A | 7.02 | 79.0 | 0.01408 | 355.2 | 5735 | 1.045 | 21.606 | 0.9168 |
| catalyst A | 7.94 | 79.0 | 0.01394 | 349.2 | | 1.070 | 22.111 | 0.9169 |
| catalyst A | 8.87 | 79.0 | 0.01362 | 337.1 | 5568 | 1.080 | 21.751 | 0.9184 |
| catalyst A | 9.93 | 79.0 | 0.01360 | 337.0 | | 1.138 | 21.984 | 0.9183 |
| catalyst A | 10.85 | 79.0 | 0.01358 | 337.3 | 6973 | 1.148 | 22.030 | 0.9187 |
| catalyst A | 11.84 | 79.0 | 0.01359 | 318.8 | | 1.037 | 21.943 | 0.9189 |
| catalyst B | 18.64 | 79.0 | 0.01808 | 262.7 | 3569 | 0.970 | 17.296 | 0.9185 |
| catalyst B | 19.67 | 79.0 | 0.01808 | 262.4 | | 1.030 | 16.889 | 0.9184 |
| catalyst B | 20.63 | 79.0 | 0.01806 | 261.8 | 3651 | 1.120 | 17.439 | 0.9184 |
| catalyst B | 21.61 | 79.0 | 0.01807 | 262.4 | | 1.131 | 17.274 | 0.9183 |
| catalyst B | 22.57 | 79.0 | 0.01806 | 262.1 | 3576 | 1.122 | 16.758 | 0.9186 |
| catalyst B | 18.64 | 79.0 | 0.01808 | 262.7 | | 0.970 | 17.296 | 0.9185 |

TABLE 2

Settings for Blown Film (1 mil, 25.4 μm)

| Resin Film Line | Exceed 1018 2.5" GEC | Catalyst A 2.5" GEC | Catalyst B 2.5" GEC |
|---|---|---|---|
| Nominal Gauge (mil) | 1.0 | 1.0 | 1.0 |
| Die Gap (mil) | 60 | 60 | 60 |
| BUR | 2.5 | 2.5 | 2.5 |
| Melt (° F.) | 403 | 399 | 400 |
| FLH (in) | 18 | 18 | 17 |
| Rate | | | |
| lb/hr | 189 | 189 | 189 |
| lb/in die | 10.05 | 10.01 | 10.02 |
| Head Pressure (psi) | 3950 | 3450 | 3570 |
| % motor load | 69.1 | 62.9 | 65.7 |
| Energy Specific Output (lb/HP/hr) | 8.56 | 9.51 | 9.15 |

TABLE 3

1 mil film property data

| Sample Identification Resin | Exceed 1018 | Catalyst A | Catalyst B | Enable 2010CB |
|---|---|---|---|---|
| Film Line | 2.5" GEC | 2.5" GEC | 2.5" GEC | 2.5" GEC |
| MI (g/10 min) | 0.94 | 1.10 | 1.10 | 0.96 |
| HLMI (g/10 mm) | 14.6 | 23.1 | 19.5 | 32.7 |
| MFR | 15.6 | 21.1 | 17.8 | 34.1 |
| Density (g/cc) | 0.9185 | 0.9180 | 0.9191 | 0.921 |
| Gauge (mils) | | | | |
| Average | 1.00 | 1.010 | 1.010 | 0.99 |
| Low | 0.89 | 0.910 | 0.900 | 0.87 |

TABLE 3-continued 1 mil film property data

| Sample Identification Resin | Exceed 1018 | Catalyst A | Catalyst B | Enable 2010CB |
|---|---|---|---|---|
| High 1% Secant (psi) | 1.09 | 1.090 | 1.090 | 1.10 |
| MD | 25,074 | 26,089 | 30,598 | 29,602 |
| TD | 25,772 | 32,445 | 36,612 | 34,867 |
| Tensile Yield Strength (psi) | | | | |
| MD | 1,363 | 1,344 | 1,615 | 1,428 |
| TD | 1,332 | 1,391 | 1,630 | 1430 |
| Elongation @ Yield (%) | | | | |
| MD | 7.0 | 6.0 | 7.7 | 6.3 |
| TD | 5.5 | 5.4 | 9.0 | 4.6 |
| Tensile Strength (psi) | | | | |
| MD | 10,457 | 10,129 | 8,375 | 8808 |
| TD | 8,644 | 8203 | 7,642 | 7393 |
| Elongation @ Break (%) | | | | |
| MD | 512 | 456 | 472 | 501 |
| TD | 658 | 688 | 694 | 724 |
| Elmendorf Tear | | | | |
| MD (gms/mil) | 247.7 | 216.4 | 102.4 | 99.4 |
| TD (gms/mil) | 408.1 | 461.2 | 560 | 627.5 |
| Dart Drop, Method A | | | | |
| Phenolic (gms/mil) | 699.5 | 618.3 | 273.8 | 172 |
| Puncture Method | | | | |
| Peak Force (lb/mil) | 12.82 | 11.05 | 13.51 | 10.84 |
| Break Energy (in-lb/mil) | 42.52 | 33.53 | 41.44 | 28.52 |
| Haze (%) | 11.2 | 9.0 | 3.7 | 8.9 |
| Gloss 45° | | | | |
| MD | 44.4 | 60.1 | 80.8 | 57.8 |
| TD | 48.2 | 65.1 | 81.6 | 63.0 |
| Average | 46.3 | 62.6 | 81.2 | 60.4 |

TABLE 4

Differential data for 1 mil films using Exceed 1018 as control

| Sample description | | Exceed control | Catalyst A | Catalyst B | Enable 2010 |
|---|---|---|---|---|---|
| Melt Temp. | (F.) | 403 | 399 | 400 | 399 |
| Head Prss | (psi) | 3950 | 3450 | 3570 | 3450 |
| % motor load | (%) | 69.1 | 62.9 | 65.7 | 62.9 |
| Spec. Output | (lb/h/rpm) | 3.13 | 3.16 | 3.17 | 3.16 |
| E. Spec. Output | (lb/hph) | 8.56 | 9.51 | 9.15 | 9.51 |
| MD Modulus | (psi) | 25,074 | 26,089 | 30,598 | 29,602 |
| TD Modulus | (psi) | 25,772 | 32,445 | 36,612 | 34,867 |
| MD Yield | (psi) | 1,363 | 1,344 | 1,615 | 1,428 |
| TD Yield | (psi) | 1,332 | 1,391 | 1,630 | 1,430 |
| MD Tensile | (psi) | 10,457 | 10,129 | 8,375 | 8,808 |
| TD Tensile | (psi) | 8,644 | 8,203 | 7,642 | 7,393 |
| Puncture PF | (lb/mil) | 12.82 | 11.05 | 13.51 | 10.84 |
| Puncture BE | (in * lb/mil) | 42.52 | 33.53 | 41.44 | 28.52 |
| MD Tear | (g/mil) | 248 | 216 | 102 | 99 |
| TD Tear | (g/mil) | 408 | 461 | 560 | 628 |
| Dart Impact | (g/mil) | 700 | 618 | 274 | 172 |
| Gloss | | 46 | 63 | 81 | 60 |
| Haze | (%) | 11.2 | 9.0 | 3.7 | 8.9 |
| (−delta F.) | Melt Temp. (−delta F.) | 0.0 | 4.0 | 3.0 | |
| (−% diff) | Head Prss (−% diff) | 0.0 | 12.7 | 9.6 | |
| (−% diff) | Motor Load (−% diff) | 0.0 | 9.0 | 4.9 | |
| (−% diff) | Specific Output (% diff) | 0.0 | 1.0 | −1.3 | |
| (% diff) | E. Spec. Output (% diff) | 0.0 | 11.1 | 6.9 | |
| (% diff) | MD Modulus (% diff) | 0.0 | 4.0 | 22.0 | 18.1 |
| (% diff) | TD Modulus (% diff) | 0.0 | 25.9 | 42.1 | 35.3 |
| (% diff) | MD Yield (% diff) | 0.0 | −1.4 | 18.5 | 4.8 |

TABLE 4-continued

Differential data for 1 mil films using Exceed 1018 as control

| Sample description | | Exceed control | Catalyst A | Catalyst B | Enable 2010 |
|---|---|---|---|---|---|
| (% diff) | TD Yield (% diff) | 0.0 | 4.4 | 22.4 | 7.4 |
| (% diff) | MD Tensile (% diff) | 0.0 | −3.1 | −19.9 | −15.8 |
| (% diff) | TD Tensile (% diff) | 0.0 | −5.1 | −11.6 | −14.5 |
| (% diff) | Puncture PF (% diff) | 0.0 | −13.8 | 5.4 | −15.4 |
| (% diff) | Puncture BE (% diff) | 0.0 | −21.1 | −2.5 | −32.9 |
| (% diff) | MD Tear (% diff) | 0.0 | −12.6 | −58.7 | −59.9 |
| (% diff) | TD Tear (% diff) | 0.0 | 13.0 | 37.2 | 53.8 |
| (% diff) | Dart Impact (% diff) | 0.0 | −11.6 | −60.9 | −75.4 |
| (% diff) | Gloss (% diff) | 0.0 | 35.2 | 75.4 | 30.5 |
| (−5X delta) | Haze (−5X delta) | 0.0 | 11.3 | 37.6 | 11.5 |

TABLE 5

Property data for 2-mil films

| Sample Identification | Exceed 1018 | Catalyst A | Catalyst B | Enable 2010CB |
|---|---|---|---|---|
| Film Line | 2.5" GEC | 2.5" GEC | 2.5" GEC | 2.5" GEC |
| Gauge (mils) | | | | |
| Average | 2.04 | 2.03 | 2.07 | 1.99 |
| Low | 1.81 | 1.88 | 2.02 | 1.83 |
| High | 2.21 | 2.14 | 2.13 | 2.11 |
| 1% Secant (psi) | | | | |
| MD | 26,166 | 26,738 | 28,423 | 29,425 |
| TD | 29,214 | 32,529 | 32,285 | 33,677 |
| Tensile Yield Strength (psi) | | | | |
| MD | 1,340 | 1,382 | 1,435 | 1,383 |
| TD | 1,432 | 1,475 | 1,479 | 1,501 |
| Elongation @ Yield (%) | | | | |
| MD | 6.3 | 7.9 | 6.8 | 6.0 |
| TD | 7.5 | 6.9 | 5.8 | 5.9 |
| Tensile Strength (psi) | | | | |
| MD | 8,431 | 7,968 | 7,501 | 7,943 |
| TD | 7,467 | 7977 | 8,194 | 7,090 |
| Elongation @ Break (%) | | | | |
| MD | 603 | 584 | 591 | 643 |
| TD | 661 | 701 | 732 | 743 |
| Elmendorf Tear | | | | |
| MD (gms/mil) | 264.5 | 232.1 | 165 | 173.3 |
| TD (gms/mil) | 358.9 | 400.4 | 509.4 | 642.2 |
| Dart Drop, Method A Phenolic (gms) | | | | |
| (gms/mil) | 628.9 | 635.0 | 363.3 | 214 |
| Puncture Method B | | | | |
| Peak Force (lb/mil) | 11.54 | 10.78 | 11.04 | 10.67 |
| Break Energy (in-lb/mil) | 40.72 | 36.20 | 37.34 | 32.0 |
| Haze (%) | 15.5 | 14.2 | 9.0 | 9.0 |
| Gloss 45° | | | | |
| MD | 45.0 | 53.6 | 66.4 | 63.1 |
| TD | 48.5 | 53.2 | 68.5 | 65.4 |
| Average | 46.8 | 53.4 | 67.5 | 64.3 |
| | | Dart maxed out | Dart maxed out | |

TABLE 6

| Differential data for 2-mil films using Exceed 1018 as control | | | | | |
|---|---|---|---|---|---|
| Sample description | | Exceed 1018 | Catalyst A | Catalyst B | Enable 2010 |
| MD Modulus | (psi) | 26,166 | 26,738 | 28,423 | 29,425 |
| TD Modulus | (psi) | 29,214 | 32,529 | 32,285 | 33,677 |
| MD Yield | (psi) | 1,340 | 1,382 | 1,435 | 1,383 |
| TD Yield | (psi) | 1,432 | 1,475 | 1,479 | 1,501 |
| MD Tensile | (psi) | 8,431 | 7,968 | 7,501 | 7,943 |
| TD Tensile | (psi) | 7,467 | 7,977 | 8,194 | 7,090 |
| Puncture PF | (lb/mil) | 11.54 | 10.78 | 11.04 | 10.67 |
| Puncture BE | (in * lb/mil) | 40.72 | 36.20 | 37.34 | 32.04 |
| MD Tear | (g/mil) | 265 | 232 | 165 | 173 |
| TD Tear | (g/mil) | 359 | 400 | 509 | 642 |
| Dart Impact | (g/mil) | 629 | 635 | 363 | 214 |
| Gloss | | 47 | 53 | 67 | 63 |
| Haze | (%) | 15.5 | 14.2 | 9.0 | 9.0 |
| Comparative Data Product Code | | Exceed control | Catalyst A | Catalyst B | Enable 2010 |
| (% diff) | MD Modulus (% diff) | 0.0 | 2.2 | 8.6 | 12.5 |
| (% diff) | TD Modulus (% diff) | 0.0 | 11.3 | 10.5 | 15.3 |
| (% diff) | MD Yield (% diff) | 0.0 | 3.1 | 7.1 | 3.2 |
| (% diff) | TD Yield (% diff) | 0.0 | 3.0 | 3.3 | 4.8 |
| (% diff) | MD Tensile (% diff) | 0.0 | −5.5 | −11.0 | −5.8 |
| (% diff) | TD Tensile (% diff) | 0.0 | 6.8 | 9.7 | −5.0 |
| (% diff) | Puncture PF (% diff) | 0.0 | −6.6 | −4.3 | −7.5 |
| (% diff) | Puncture BE (% diff) | 0.0 | −11.1 | −8.3 | −21.3 |
| (% diff) | MD Tear (% diff) | 0.0 | −12.2 | −37.6 | −34.5 |
| (% diff) | TD Tear (% diff) | 0.0 | 11.6 | 41.9 | 78.9 |
| (% diff) | Dart Impact (% diff) | 0.0 | 1.0 | −42.2 | −66.0 |
| (% diff) | Gloss (% diff) | 0.0 | 11.6 | 41.9 | 78.9 |
| (−5X delta) | Haze (−5X delta) | 0.0 | 6.5 | 32.6 | 32.3 |

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A catalyst composition comprising a catalyst compound supported to form a supported catalyst system, wherein the catalyst compound comprises:

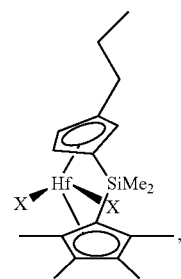

wherein each X is independently a leaving group selected from a halogen, a labile hydrocarbyl, a substituted hydrocarbyl, or a heteroatom group.

2. The catalyst composition of claim 1, comprising an activator comprising an acid derived from a weakly coordinating anion.

3. The catalyst composition of claim 2, wherein the activator comprises an aluminoxane compound, an organoboron, an organoaluminum compound or combinations thereof.

4. The catalyst composition of claim 2, wherein the activator comprises methyl aluminoxane or modified methylauminoxane.

5. The catalyst composition of claim 1, comprising a support comprising a mineral, a clay, a metal oxide, a metalloid oxide, a mixed metal oxide, a mixed metalloid oxide, a mixed metal-metalloid oxide, a polymer, or any combinations thereof.

6. The catalyst composition of claim 5, wherein the support is a polyolefin or a polyolefin derivative.

7. The catalyst composition of claim 5, wherein the support has been thermally treated and/or chemically treated with an acid, an organoaluminum, or a fluoriding agent, or any combinations thereof.

8. The catalyst composition of claim 5, wherein the support has been thermally treated.

9. The catalyst composition of claim 5, wherein the support comprises silica, alumina, aluminosilicate, titanated silica, or titanated alumina, or any combinations thereof.

10. The catalyst composition of claim 1, comprising a silica support and a methyl aluminoxane activator.

\* \* \* \* \*